United States Patent
Kobayakawa et al.

(10) Patent No.: US 9,918,472 B2
(45) Date of Patent: *Mar. 20, 2018

(54) ANIMAL REPELLENT

(71) Applicant: SCENT SCIENCE INTERNATIONAL INC., Osaka-shi, Osaka (JP)

(72) Inventors: Ko Kobayakawa, Suita (JP); Reiko Kobayakawa, Suita (JP)

(73) Assignee: Scent Science International Inc., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/924,927

(22) Filed: Oct. 28, 2015

(65) Prior Publication Data
US 2016/0113279 A1 Apr. 28, 2016

Related U.S. Application Data

(63) Continuation of application No. 13/577,609, filed as application No. PCT/JP2011/052652 on Feb. 8, 2011, now Pat. No. 9,198,427.

(30) Foreign Application Priority Data

Feb. 8, 2010 (JP) .................................. 2010-025681
Jul. 30, 2010 (JP) .................................. 2010-172671

(51) Int. Cl.
| A01N 43/84 | (2006.01) |
| A01N 31/02 | (2006.01) |
| A01N 43/10 | (2006.01) |
| A01N 43/78 | (2006.01) |
| A01N 47/46 | (2006.01) |
| A01N 37/02 | (2006.01) |
| A01N 43/86 | (2006.01) |

(52) U.S. Cl.
CPC ............. *A01N 43/84* (2013.01); *A01N 31/02* (2013.01); *A01N 37/02* (2013.01); *A01N 43/10* (2013.01); *A01N 43/78* (2013.01); *A01N 43/86* (2013.01); *A01N 47/46* (2013.01)

(58) Field of Classification Search
CPC ...................................................... A01N 43/78
See application file for complete search history.

(56) References Cited

U.S. PATENT DOCUMENTS

| 2,411,253 | A | 11/1946 | Flenner et al. |
| 4,440,783 | A | 4/1984 | Downing |
| 5,672,352 | A | 9/1997 | Clark et al. |
| 5,973,162 | A | 10/1999 | Alig et al. |
| 6,747,047 | B2 | 6/2004 | Lahm et al. |
| 9,198,427 | B2 * | 12/2015 | Kobayakawa ......... A01N 31/02 |
| 2003/0229050 | A1 | 12/2003 | Lahm et al. |

FOREIGN PATENT DOCUMENTS

| JP | 64-038003 A | 2/1989 |
| JP | 07-285821 A | 10/1995 |
| JP | 08-239305 A | 9/1996 |
| JP | 2001-064102 A | 3/2001 |
| JP | 2001-158712 A | 6/2001 |
| JP | 2002-173401 A | 6/2002 |
| JP | 2009-120550 A | 6/2009 |
| RU | 2278852 C2 | 6/2006 |
| SU | 845754 A3 | 7/1981 |
| WO | WO 2008/083038 A1 | 7/2008 |

OTHER PUBLICATIONS

Burwash et al., *Journal of Chemical Ecology*, 24(1): 49-66 (1998).
Fendt et al., *Neurosci. Biobehav. Rev.*, 29: 1145-1156 (2005).
Fendt et al., *Neurosci. Biobehav. Rev.*, 32: 1259-1266 (2008).
Kobayakawa et al., *Nature*, 450: 503-508 (2007).
Kobayakawa et al., *Cell Technology*, 27 (11): 1131-1138 (Nov. 2008).
Kobayakawa et al., *Aroma Research*, 10 (3): 282-288 (2009).
Kobayakawa, Ko, *Journal of Japan Foundation of Applied Enzymology*, 2010 (44): 73-74 (2010).
Osada et al., *Chemical Senses*, 33(9): 815-823 (Nov. 1, 2008).
Schafer et al., *Archives of Environmental Contamination and Toxicology*, 12 (3): 355-382 (1983).
Schafer et al., *Archives of Environmental Contamination and Toxicology*, 14: 111-129 (1985).
Starr et al., *Agricultural and Food Chemistry*, 12(4): 342-344 (1964).

(Continued)

*Primary Examiner* — Sreeni Padmanabhan
*Assistant Examiner* — Jody Karol
(74) *Attorney, Agent, or Firm* — Leydig, Voit & Mayer, Ltd.

(57) ABSTRACT

The invention provides an animal repellent containing, as an active ingredient, a compound having an odor innately inducing fear in animals, which is free from acclimation of animals to the aforementioned odor. The active ingredient is at least one kind selected from a heterocyclic compound represented by the formula (1):

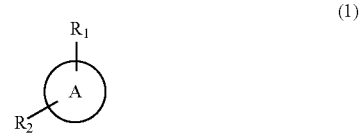

(1)

wherein ring A is a 3- to 7-membered heterocycle containing at least one hetero atom selected from a nitrogen atom, a sulfur atom and an oxygen atom, and $R_1$ and $R_2$ are each independently hydrogen, a halogen atom, an optionally substituted alkyl group, an optionally substituted alkoxy group, an acyl group, an optionally esterified carboxyl group, an optionally substituted thiol group, an optionally substituted amino group or an oxo group, or a salt thereof, a chain sulfide compound and alkyl isothiocyanate.

15 Claims, 5 Drawing Sheets

(56) References Cited

OTHER PUBLICATIONS

Tokyo Kasei Organic Chemicals (Laboratory Organics Fine & Specialty Organics Mfg.), TCI Catalog 34, pp. 248, 618, 619, 729, 1072, 1074, 1408, 1415 (1998).
Vernet-Maury, "Trimethyl-thiazoline in fox feces: a natural alarming substance for the Rat," *Olfaction and Taste VII: Proceedings of the Seventh International Symposium on Olfaction and Taste and of the Fourth Congress of the European Chemoreception Research Organization*, Edited by H. van der Starre (IPL Press Ltd.), p. 407 (1980).
Vernet-Maury et al., *J. Chem. Ecol.*, 10: 1007-1018 (1984).
European Patent Office, Extended European Search Report in European Patent Application 11739922.0 (dated Oct. 22, 2013).
Japanese Patent Office, International Search Report in International Patent Application No. PCT/JP2011/052652 (dated Mar. 8, 2011).
Japanese Patent Office, International Preliminary Report on Patentability in International Patent Application No. PCT/JP2011/052652 (dated Jun. 7, 2012).
Spurr et al., *Pest Management Science*, 57(7): 615-619 (2001).
Szolcsányi et al., *Pain*, 27(2): 247-260 (1986).

\* cited by examiner

ANIMAL REPELLENT

CROSS-REFERENCE TO RELATED APPLICATIONS

This patent application is a continuation of copending U.S. patent application Ser. No. 13/577,609, filed Sep. 19, 2012, which is the U.S. national phase of International Patent Application No. PCT/JP2011/052652, filed Feb. 8, 2011, which claims the benefit of Japanese Patent Application No. 2010-025681, filed Feb. 8, 2010, and Japanese Patent Application No. 2010-172671, filed Jul. 30, 2010, which are incorporated by reference in their entireties herein.

TECHNICAL FIELD

The present invention relates to an animal repellent containing, as an active ingredient, a compound having an odor innately inducing fear in animals.

BACKGROUND ART

Conventionally, various problems caused by wild animals, such as damage on farm products due to the intrusion of animals into agricultural lands, accident due to the intrusion of animals into roads and railroads, damage due to the intrusion of animals into residence, damage such as bite damage on electric cables and communication cable networks and the like, accident by collision of bird with airplane and the like, are producing loss in life and loss in economy.

As a countermeasure for such damages caused by animals, various repellents are disclosed (patent documents 1, 2 and 3). Many of these repellents take note of odorants. However, since such repellents simply have an odor that the animals hate, they are considered to lose effect by habituation.

On the other hand, it is empirically known that an odor developed from excretion, secretion and the like of carnivorous animals induces an avoidance behavior of animals. Taking note of this effect, methods using the excretion itself of carnivorous animals as an animal repellent have been proposed and, for example, a product using urine itself of gray wolf (*Canis lupus*) as a repellent has been imported and sold. However, it is not easy to produce a large amount of the excretion of endangered animals such as wolf and the like.

An example of a specified odorant molecule inducing an avoidance behavior is 2,4,5-trimethyl-3-thiazoline (TMT). TMT was separated and identified as a component inducing a fear response, from the odor components secreted from the anal gland of fox, which is a natural enemy of rodent animals such as mouse, rat and the like. E. Vernet-Maury et al. analyzed the odor components contained in the feces of fox, and analyzed 70 kinds of odorant molecules for the effect on animals. As a result, an odorant molecule having the strongest effect was TMT (non-patent document 1).

Furthermore, Maury et al. analyzed the effect of 11 kinds of odorant molecules having chemical structures similar to that of TMT. However, their effects were equal to or less than that of TMT (non-patent document 2).

Based on these experimental results, TMT has been widely studied as a sole substance that induces fear in animals and shows a repellent action. However, its action is not clear, and induces only a weak response as compared to the odor of a natural enemy itself. Therefrom a question has been raised if TMT does not induce a fear reaction to a natural enemy but is simply recognized as a bad smell (non-patent documents 3 and 4). Alternatively, it is considered that the odor of natural enemy itself contains a mixture of odors of many compounds and a single compound cannot reproduce the effect.

Using the genetic engineering, the present inventors generated a neural circuit-modified mouse by intentionally removing a part of the olfactory neural circuit that processes the odor information, and conducted a unique study by analyzing the behaviors of the mutant mouse that smelled the odor, whereby to elucidate the biological function of individual olfactory neural circuits. As a result, they have clarified for the first time in the world that a fear reaction of a mouse to a natural enemy odor and an aversive response to a putrid odor are respectively and innately controlled by the olfactory neural circuit present in a particular intracerebral area (non-patent documents 5 and 6).

Therefrom it has been elucidated that TMT is a substance that induces fear in animals. However, TMT still shows a lower repellent effect as compared to that provided by the odor of a natural enemy itself, and a single substance having a repellent effect exceeding that of TMT has not been found as yet.

DOCUMENT LIST

Patent Documents patent document 1: JP-A-2001-158712
patent document 2: JP-A-2002-173401
patent document 3: JP-A-2009-120550

Non-Patent Documents non-patent document 1: Vernet-Maury, "Trimethyl-thiazoline in fox feces: a natural alarming substance for the Rat," *Olfaction and Taste VII: Proceedings of the Seventh International Symposium on Olfaction and Taste and of the Fourth Congress of the European Chemoreception Research Organization*, Edited by H. van der Starre (IPL Press Ltd.), page 407 (1980)
non-patent document 2: J. Chem. Ecol. 10: 1007-1018 (1984)
non-patent document 3: Neurosci. Biobehav. Rev. 29: 1145-1156 (2005)
non-patent document 4: Neurosci. Biobehav. Rev. 32: 1259-1266 (2008)
non-patent document 5: Nature 450: 503-508 (2007)
non-patent document 6: Cell Technology, Vol. 27, No. 11, pp. 1131-1138, November 2008

SUMMARY OF THE INVENTION

Problems to be Solved by the Invention

The present invention aims to provide an animal repellent containing, as an active ingredient, a compound having an odor innately inducing fear in animals, which is useful for preventing damages caused by harmful animals including small animals such as mouse and the like, and free from acclimation of animals to the aforementioned odor. The active ingredient is required to provide an effect superior to that of TMT conventionally considered to induce fear in animals.

Means of Solving the Problems

The present inventors have conducted intensive studies in an attempt to solve the aforementioned problems and found that particular compounds induce strong fear in animals and can be utilized as active ingredients of a repellent, which resulted in the completion of the present invention.

Accordingly, the present invention provides (1) an animal repellent comprising, as an active ingredient, at least one kind selected from a heterocyclic compound represented by the formula (1):

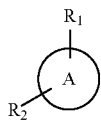
(1)

wherein
ring A is a 3- to 7-membered heterocycle containing at least one hetero atom selected from a nitrogen atom, a sulfur atom and an oxygen atom, and
$R_1$ and $R_2$ are each independently hydrogen, a halogen atom, an optionally substituted alkyl group, an optionally substituted alkoxy group, an acyl group, an optionally esterified carboxyl group, an optionally substituted thiol group, an optionally substituted amino group or an oxo group, or a salt thereof, a chain sulfide compound and alkyl isothiocyanate;

(2) the animal repellent of (1), wherein ring A is pyrrole, pyridine, pyridazine, pyrimidine, pyrazine, piperazine, pyrrolidine, hexahydropyridazine, imidazolidine, piperidine, ethylene sulfide, trimethylene sulfide, thiophene, thiolane, tetrahydro-2H-thiopyran, thiazoline, thiazole, thiazolidine, isothiazole, isothiazoline, thiomorpholine, thiadiazoline, thiadiazole, thiadiazolidine, 1,3-thiazane, 5,6-dihydro-4H-1,3-thiazine, furan, 2H-pyran, 4H-pyran, oxazole, isoxazole, morpholine or oxazoline;

(3) the animal repellent of (1) or (2), wherein ring A is a 3- to 7-membered heterocycle containing a nitrogen atom and/or a sulfur atom;

(4) the animal repellent of (1) or (2), wherein ring A is a 3- to 7-membered heterocycle containing a nitrogen atom and a sulfur atom;

(5) an animal repellent comprising, as an active ingredient, a compound selected from the compounds represented by the formulas (A) to (H):

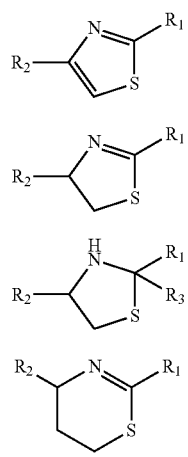

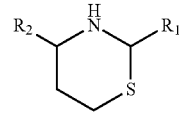
(E)

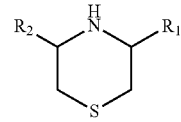
(F)

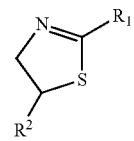
(G)

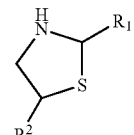
(H)

wherein
$R_1$, $R_2$ and $R_3$ are each independently hydrogen, a halogen atom, an optionally substituted alkyl group, an optionally substituted alkoxy group, an acyl group, an optionally esterified carboxyl group, an optionally substituted thiol group, an optionally substituted amino group or an oxo group, provided that $R_1$ and $R_2$ in the formula (A) are not oxo groups, $R_1$ in the formula (B), the formula (D) and the formula (G) is not an oxo group, and $R_1$ and $R_3$ in the formula (C) may together form an oxo group, or a salt thereof;

(6) the animal repellent of (5), wherein said compound is a compound represented by the formula (A);

(7) the animal repellent of (5), wherein said compound is a compound represented by the formula (B) or the formula (C);

(8) the animal repellent of (6), wherein said compound is a compound selected from 2-methylthiazole, 2-ethylthiazole, 2-bromothiazole, 4-methylthiazole and 2,4-dimethylthiazole;

(9) the animal repellent of (7), wherein said compound is a compound selected from 2-methyl-2-thiazoline, 2-methylthio-2-thiazoline, 4-methyl-2-thiazoline, 2,4-dimethyl-2-thiazoline and 2,2-dimethylthiazolidine;

(10) the animal repellent of (5), wherein said compound is a compound represented by the formula (F);

(11) the animal repellent of (5), wherein said compound is a compound represented by the formula (G);

(12) the animal repellent of (10), wherein said compound is thiomorpholine;

(13) the animal repellent of (11), wherein said compound is a compound selected from 2,5-dimethyl-2-thiazoline and 5-methyl-2-thiazoline;

(14) the animal repellent of (1), wherein the chain sulfide compound is allyl methyl sulfide;

(15) the animal repellent of (1), wherein alkyl isothiocyanate is ethyl isothiocyanate;

(16) the animal repellent of any one of (1) to (15), which is used for a harmful animal;

(17) a method for repelling an animal, comprising placing at least one kind selected from a heterocyclic compound represented by the formula (1) or a salt thereof, a chain sulfide compound and alkyl isothiocyanate in a space from which the animal is repelled;

(18) a method for repelling an animal, comprising placing a compound selected from the compounds represented by the formulas (A) to (H) or a salt thereof in a space from which the animal is repelled;

(19) at least one kind of compound selected from a heterocyclic compound represented by the formula (1) or a salt thereof, a chain sulfide compound and alkyl isothiocyanate for use as an animal repellent;

(20) a compound selected from the compounds represented by the formulas (A) to (H) or a salt thereof for use as an animal repellent;

(21) use of at least one kind of compound selected from a heterocyclic compound represented by the formula (1) or a salt thereof, a chain sulfide compound and alkyl isothiocyanate as an animal repellent; and

(22) use of a compound selected from the compounds represented by the formulas (A) to (H) or a salt thereof as an animal repellent.

Effect of the Invention

According to the present invention, a repellent having a strong repellent action on harmful animals can be obtained. Since the repellent of the present invention has an odor that induces strong innate fear in harmful animals, the animals do not show acclimation to the odor of the repellent of the present invention. Thus, the possibility of the effect of the repellent decreasing by habituation is low.

The expression "induces innate fear" includes activation of a neural circuit that innately induces fear (including, for example, olfactory neural circuit, vomeronasal neural circuit). Specifically, it includes induction of a fear behavior (e.g., freezing behavior, escape behavior and the like due to fear) in a particular animal to an animal that can be a natural enemy. The "odor" can be used to mean the same as smell. The odor in the present invention includes stimulation felt by the nose of an animal, which induces aversion, fear, alienation or avoidance behavior and the like in the animal, and the like. The odor includes an odor that activates neural circuit inducing fear (including, for example, olfactory neural circuit, vomeronasal neural circuit). The expression "animals do not show acclimation to the odor" means that even with repeated odor stimulation for an animal, the fear behavior (e.g., freezing behavior, escape behavior and the like) of the animal does not disappear or decrease, and the repellent effect continues. The term "repel" used here means dislike and avoid and includes, for example, aversion, fear, alienation or avoidance.

DESCRIPTION OF EMBODIMENTS

Figure 1:
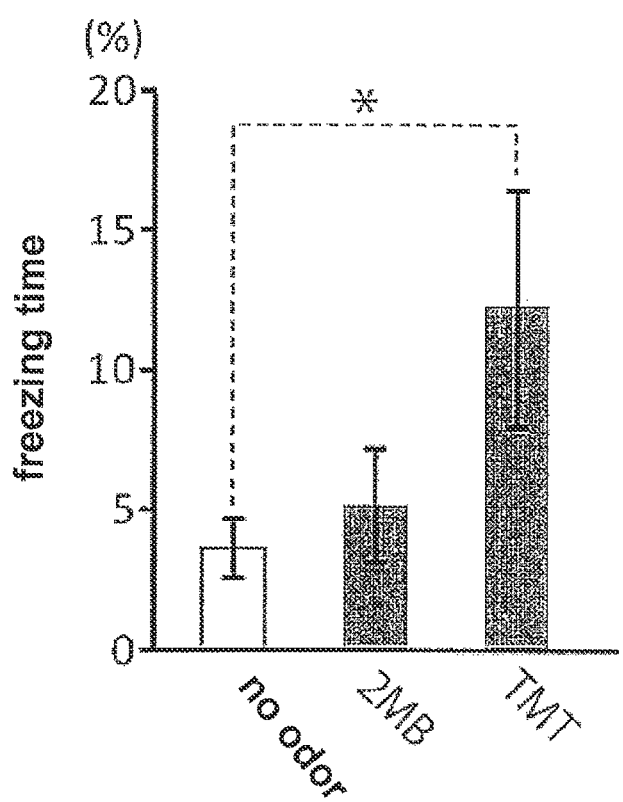
FIG. 1 shows the results of freezing tests using 2-methylbutyric acid producing a putrid odor and TMT inducing a sense of fear.

Ring A in the formula (1) is a 3- to 7-membered heterocycle containing at least one (preferably 1 to 3, more preferably 1 or 2) hetero atoms selected from a nitrogen atom, a sulfur atom and an oxygen atom. Ring A is preferably a 3- to 7-membered heterocycle containing a nitrogen atom and/or a sulfur atom. Ring A is more preferably a 3- to 7-membered heterocycle containing a nitrogen atom and a sulfur atom. The member of ring A is preferably 3 to 6, more preferably 5 or 6.

Examples of the aforementioned heterocycle includes, but are not limited to, pyrrole, pyridine, pyridazine, pyrimidine, pyrazine, piperazine, pyrrolidine, hexahydropyridazine, imidazole, imidazolidine, piperidine, ethylene sulfide, trimethylene sulfide, thiophene, thiolane, tetrahydro-2H-thiopyran, thiazoline (e.g., 2-thiazoline, 3-thiazoline, 4-thiazoline), thiazole, thiazolidine, isothiazole, isothiazoline, thiomorpholine, thiadiazoline, thiadiazole, thiadiazolidine, 1,3-thiazane, 5,6-dihydro-4H-1,3-thiazine, furan, 2H-pyran, 4H-pyran, oxazole, isoxazole, morpholine, oxazoline and the like. Preferred are thiazoline (e.g., 2-thiazoline), thiazole, thiazolidine, isothiazole, isothiazoline, thiomorpholine, thiadiazoline, thiadiazole, thiadiazolidine, 1,3-thiazane and 5,6-dihydro-4H-1,3-thiazine, more preferably, thiazoline (e.g., 2-thiazoline), thiazole, thiazolidine, 1,3-thiazane, 5,6-dihydro-4H-1,3-thiazine and thiomorpholine.

The "halogen atom" used here is preferably selected from fluorine, chlorine, bromine and iodine.

The term "alkyl group" used here (when used as a group or a part of a group) is a straight chain or branched chain alkyl group having carbon atoms in the designated number. Examples of the alkyl group include a $C_{1-6}$ alkyl group, preferably a $C_{1-4}$ alkyl group. The $C_{1-6}$ alkyl group means a straight chain or branched chain alkyl group having 1 to 6 carbon atoms. Examples of the $C_{1-6}$ alkyl group include, but are not limited to, methyl group, ethyl group, propyl group, isopropyl group, butyl group, 1-methylpropyl group, 2-methylpropyl group, tert-butyl group, pentyl group, 1-methylbutyl group, 2-methylbutyl group, 3-methylbutyl group, 1,1-dimethylpropyl group, 2,2-dimethylpropyl group, 1,2-dimethylpropyl group, 1-ethylpropyl group, hexyl group, 1-methylpentyl group, 2-methylpentyl group, 3-methylpentyl group, 4-methylpentyl group, 1,1-dimethylbutyl group, 2,2-dimethylbutyl group, 3,3-dimethylbutyl group, 1,2-dimethylbutyl group, 1,3-dimethylbutyl group, 2,3-dimethylbutyl group, 1-ethylbutyl group, 2-ethylbutyl group and 1-ethyl-2-methylpropyl group. Preferable examples of the alkyl group include straight chain or branched chain alkyl group having a carbon number of 1 to 4. More preferred are methyl group, ethyl group, propyl group, isopropyl group, butyl group and isobutyl group, and particularly preferred is methyl group.

The aforementioned alkyl group may be substituted, and examples of the substituent include a halogeno group and the like. As the halogeno group, a fluoro group, a chloro group, a bromo group and the like can be mentioned. The $C_{1-6}$ haloalkyl group means a $C_{1-6}$ alkyl group substituted by 1 to 5 halogeno groups. When two or more halogeno groups are present, the kind of respective halogeno groups may be the same or different. Examples of the $C_{1-6}$ haloalkyl group include fluoromethyl group, difluoromethyl group, trifluoromethyl group, chlorodifluoromethyl group, 1-fluoroethyl group, 2-fluoroethyl group, 2-chloroethyl group, 2-bromoethyl group, 1,1-difluoroethyl group, 1,2-difluoroethyl group, 2,2,2-trifluoroethyl group, 1,1,2,2-tetrafluoroethyl group, 1,1,2,2,2-pentafluoroethyl group, 1-fluoropropyl group, 1,1-difluoropropyl group, 2,2-difluoropropyl group, 3-fluoropropyl group, 3,3,3-trifluoropropyl group, 4-fluorobutyl group, 4,4,4-trifluorobutyl group, 5-fluoropentyl group, 5,5,5-trifluoropentyl group, 6-fluorohexyl group, 6,6,6-trifluorohexyl group and the like.

The term "alkoxy group" used here (when used as a group or a part of a group) shows a —O(alkyl) group having carbon atoms in the designated number. Examples of the alkoxy group include a $C_{1-6}$ alkoxy group. Examples of the $C_{1-6}$ alkoxy group include, but are not limited to, methoxy group, ethoxy group, propoxy group, isopropoxy group, butoxy group, 1-methylpropoxy group, 2-methylpropoxy group, tert-butoxy group, pentyloxy group, 1-methylbutoxy group, 2-methylbutoxy group, 3-methylbutoxy group, 1,1-dimethylpropoxy group, 2,2-dimethylpropoxy group, 1,2-dimethylpropoxy group, 1-ethylpropoxy group, hexyloxy group, 1-methylpentyloxy group, 2-methylpentyloxy group, 3-methylpentyloxy group, 4-methylpentyloxy group, 1,1-dimethylbutoxy group, 2,2-dimethylbutoxy group, 3,3-dimethylbutoxy group, 1,2-dimethylbutoxy group, 1,3-dimethylbutoxy group, 2,3-dimethylbutoxy group, 1-ethylbutoxy group, 2-ethylbutoxy group, 1-ethyl-2-methylpropoxy group and the like.

The aforementioned alkoxy group may be substituted, and examples of the substituent include a halogeno group and the like. As the halogeno group, the same substituents as those for the above-mentioned alkyl group can be mentioned. The $C_{1-6}$ haloalkoxy group means a $C_{1-6}$ alkoxy group substituted by 1 to 5 halogeno groups. When the number of the halogeno group is two or more, the kinds of the halogeno groups may be the same or different. Examples of the $C_{1-6}$ haloalkoxy group include fluoromethoxy group, difluoromethoxy group, trifluoromethoxy group, 1-fluoroethoxy group, 2-fluoroethoxy group, 2-chloroethoxy group, 2-bromoethoxy group, 1,1-difluoroethoxy group, 1,2-difluoroethoxy group, 2,2,2-trifluoroethoxy group, 1,1,2,2-tetrafluoroethoxy group, 1,1,2,2,2-pentafluoroethoxy group, 1-fluoropropoxy group, 1,1-difluoropropoxy group, 2,2-difluoropropoxy group, 3-fluoropropoxy group, 3,3,3-trifluoropropoxy group, 2,2,3,3,3-pentafluoropropoxy group, 4-fluorobutoxy group, 4,4,4-trifluorobutoxy group, 5-fluoropentyloxy group, 5,5,5-trifluoropentyloxy group, 6-fluorohexyloxy group, 6,6,6-trifluorohexyloxy group and the like.

Examples of the "acyl group" used here include a formyl group and a $C_{1-6}$ alkyl-carbonyl group. Examples of the $C_{1-6}$ alkyl-carbonyl group include, but are not limited to, acetyl group, propionyl group, butyryl group, isobutyryl group, valeryl group, hexanoyl group and the like.

The term "carboxyl group" used here (when used as a group or a part of a group) shows a —COOH group. The aforementioned carboxyl group may be esterified. Specific examples of the optionally esterified carboxyl group include carboxyl group and $C_{1-6}$ alkoxycarbonyl group. The $C_{1-6}$ alkoxy moiety of the $C_{1-6}$ alkoxycarbonyl group means the same as the $C_{1-6}$ alkoxy group of the optionally substituted alkoxy group.

The term "thiol group" used here (when used as a group or a part of a group) shows a —SH group. The aforementioned thiol group may be substituted, and examples of the substituent include a $C_{1-6}$ alkyl group and the like. The $C_{1-6}$ alkyl group means the same as the $C_{1-6}$ alkyl group of the optionally substituted alkyl group. Specific examples of the optionally substituted thiol group include a thiol group and a $C_{1-6}$ alkylthio group. Examples of the $C_{1-6}$ alkylthio group include, but are not limited to, methylthio group, ethylthio group, propylthio group, butylthio group and the like.

The term "amino group" used here (when used as a group or a part of a group) shows a —NH$_2$ group. The aforementioned amino group may be substituted by 1 or 2 substituents, and examples of the substituent include a $C_{1-6}$ alkyl group, —COR$_5$ (wherein R$_5$ is hydrogen or a $C_{1-6}$ alkyl group) and the like. The $C_{1-6}$ alkyl group means the same as the $C_{1-6}$ alkyl group of the optionally substituted alkyl group. Specific examples of the optionally substituted amino group include amino group, $C_{1-6}$ alkylamino group, di($C_{1-6}$ alkyl)amino group and —NR$_4$COR$_5$ wherein R$_4$ and R$_5$ are each independently hydrogen or $C_{1-6}$ alkyl group. Examples of the $C_{1-6}$ alkylamino group include, but are not limited to, methylamino group, ethylamino group, 1-methylethylamino group and the like, and examples of the di($C_{1-6}$ alkyl)amino group include, but are not limited to, dimethylamino group, N-ethyl-N-methylamino group, bis(1-methylethyl)amino group and the like.

The term "oxo" used here (when used as a group or a part of a group) shows a =O group.

Examples of the preferable heterocyclic compound used as an active ingredient of the repellent of the present invention include, but are not limited to, thiazole, 2-methylthiazole, 2-ethylthiazole, 2-bromothiazole, 4-methylthiazole, 2-formylthiazole, 2-aminothiazole, 5-methylthiazole, 2,4-dimethylthiazole, 4,5-dimethylthiazole, 2-thiazoline, 2-methyl-2-thiazoline, 2-ethyl-2-thiazoline, 2-bromo-2-thiazoline, 2,4-dimethyl-2-thiazoline, 4-methyl-2-thiazoline, 2-methylthio-2-thiazoline, 2-methyl-4-ethyl-2-thiazoline, 2-amino-2-thiazoline, 5-methyl-2-thiazoline, 4,5-dimethyl-2-thiazoline, 2,5-dimethyl-2-thiazoline, 2-mercapto-2-thiazoline, 2-propyl-2-thiazoline, 2-(1-methylethyl)-2-thiazoline, 2-(1-methylpropyl)-2-thiazoline, thiazolidine, 2-methylthiazolidine, 4-methylthiazolidine, 5-methylthiazolidine, 2,4-dimethylthiazolidine, 2,2-dimethylthiazolidine, 2,5-dimethylthiazolidine, 4,5-dimethylthiazolidine, 2,4,5-trimethylthiazolidine, 1,3-thiazane, 5,6-dihydro-4H-1,3-thiazine, 2-methyl-2-oxazoline, 2-ethyl-2-oxazoline, 2-isopropyl-2-oxazoline, 2-propyl-2-oxazoline, 2,4,4-trimethyl-2-oxazoline, 4,4-dimethyl-2-oxazoline, oxazole, thiophene, thiolane (tetrahydrothiophene), imidazole, thiomorpholine, morpholine, isobutylene sulfide and the like.

Other preferable embodiments of the heterocyclic compound used as an active ingredient of the repellent of the present invention include thiazole, thiazoline and thiazolidine, wherein the 2-position and/or the 4-position, or the 2-position and/or the 5-position are substituted, from among the heterocyclic compounds represented by the aforementioned formulas (A) to (H), as well as thiophene and thiomorpholine, and the like. Such heterocyclic compounds include substances generally known as reagents, commercially available ones can be utilized, and they can be obtained by a method known per se. However, use of the particular thiazole, thiazoline, thiazolidine, thiophene and thiomorpholine derivatives of the present invention as animal repellents has never been disclosed or suggested.

A preferable example of the compounds represented by the formulas (A) to (H) is
a compound selected from the compounds represented by the formulas (A) to (H):

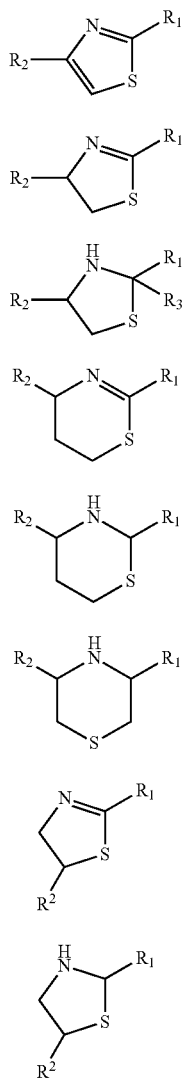

(A)
(B)
(C)
(D)
(E)
(F)
(G)
(H)

wherein

R$_1$, R$_2$ and R$_3$ are each independently hydrogen, a halogen atom, a C$_{1-6}$ alkyl group, a C$_{1-6}$ haloalkyl group, a C$_{1-6}$ alkoxy group, a C$_{1-6}$ haloalkoxy group, a formyl group, a C$_{1-6}$ alkyl-carbonyl group, a carboxyl group, a C$_{1-6}$ alkoxycarbonyl group, a thiol group, a C$_{1-6}$ alkylthio group, an amino group, a C$_{1-6}$ alkylamino group, a di(C$_{1-6}$ alkyl)amino group, —NR$_4$COR$_5$ or an oxo group, and R$_4$ and R$_5$ are each independently hydrogen or a C$_{1-6}$ alkyl group, provided that R$_1$ and R$_2$ in the formula (A) are not oxo groups, R$_1$ in the formula (B), the formula (D) and the formula (G) is not an oxo group, and R$_1$ and R$_3$ in the formula (C) may together form an oxo group, or a salt thereof.

A more preferable example of the compounds represented by the formulas (A) to (H) is a compound selected from the compounds represented by the formulas (A) to (H):

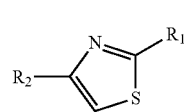
(A)
(B)
(C)
(D)
(E)
(F)

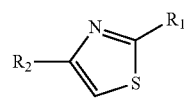
(G)

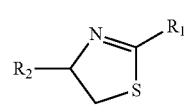
(H)

wherein

R$_1$, R$_2$ and R$_3$ are each independently hydrogen, a halogen atom, a C$_{1-6}$ alkyl group or a C$_{1-6}$ alkylthio group, or a salt thereof.

A preferable example of the compounds represented by the formulas (A) to (E) is a compound selected from the compounds represented by the formulas (A) to (E):

(A)
(B)
(C)

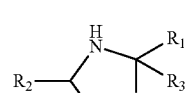

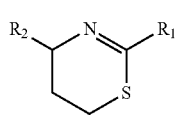 (D)

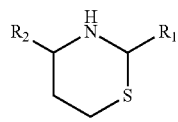 (E)

wherein
  $R_1$, $R_2$ and $R_3$ are each independently hydrogen, a halogen atom, a $C_{1-6}$ alkyl group, a $C_{1-6}$ haloalkyl group, a $C_{1-6}$ alkoxy group, a $C_{1-6}$ haloalkoxy group, a formyl group, a $C_{1-6}$ alkyl-carbonyl group, a carboxyl group, a $C_{1-6}$ alkoxycarbonyl group, a thiol group, a $C_{1-6}$ alkylthio group, an amino group, a $C_{1-6}$ alkylamino group, a di($C_{1-6}$ alkyl)amino group, —$NR_4COR_5$ or an oxo group, and
  $R_4$ and $R_5$ are each independently hydrogen or a $C_{1-6}$ alkyl group,
  provided that $R_1$ and $R_2$ in the formula (A) are not oxo groups, $R_1$ in the formula (B) and the formula (D) is not an oxo group, and $R_1$ and $R_3$ in the formula (C) may together form an oxo group,
or a salt thereof.

A more preferable example of the compounds represented by the formulas (A) to (E) is
a compound selected from the compounds represented by the formulas (A) to (E):

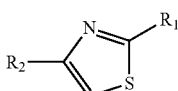 (A)

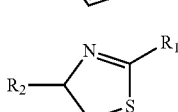 (B)

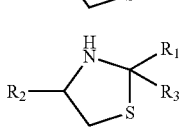 (C)

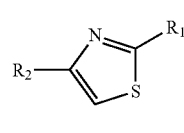 (D)

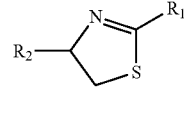 (E)

wherein
  $R_1$, $R_2$ and $R_3$ are each independently hydrogen, a halogen atom, a $C_{1-6}$ alkyl group or a $C_{1-6}$ alkylthio group,
or a salt thereof.

A particularly preferable example of the compounds represented by the formulas (A) to (C) is
a compound selected from the compounds represented by the formulas (A) to (C):

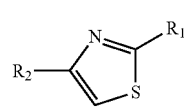 (A)

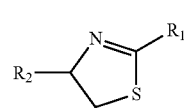 (B)

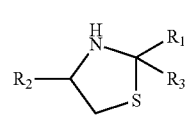 (C)

wherein
  $R_1$, $R_2$ and $R_3$ are each independently hydrogen, a halogen atom, a $C_{1-6}$ alkyl group or a $C_{1-6}$ alkylthio group, or a salt thereof.

In the formulas (A) to (C), a compound wherein
  $R_1$ is hydrogen, a halogen atom (e.g., bromine atom), a $C_{1-6}$ alkyl group (e.g., methyl, ethyl) or a $C_{1-6}$ alkylthio group (e.g., methylthio),
  $R_2$ is hydrogen or a $C_{1-6}$ alkyl group (e.g., methyl), and
  $R_3$ is hydrogen or a $C_{1-6}$ alkyl group (e.g., methyl), or a salt thereof is more preferable.

In the formulas (A) to (C), a compound wherein
  $R_1$, $R_2$ and $R_3$ are each independently hydrogen or a $C_{1-6}$ alkyl group (e.g., methyl, ethyl), or a salt thereof is more preferable.

Another preferable embodiment of the heterocyclic compound used as an active ingredient of the repellent of the present invention is a compound represented by the formula (A) or (B):

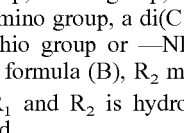 (A)

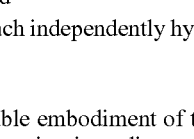 (B)

wherein
  $R_1$ and $R_2$ are each independently hydrogen, a halogen atom, a $C_{1-6}$ alkyl group, a $C_{1-6}$ alkoxy group, a formyl group, a $C_{1-6}$ alkyl-carbonyl group, a carboxyl group, an amino group, a thiol group, a $C_{1-6}$ haloalkyl group, a $C_{1-6}$ alkylamino group, a di($C_{1-6}$ alkyl)amino group, a $C_{1-6}$ alkylthio group or —$NR_4COR_5$, in the compound of the formula (B), $R_2$ may be an oxo group,
  when one of $R_1$ and $R_2$ is hydrogen, the other is not hydrogen, and
  $R_4$ and $R_5$ are each independently hydrogen or a $C_{1-6}$ alkyl group
or a salt thereof.

Another preferable embodiment of the heterocyclic compound used as an active ingredient of the repellent of the present invention is a compound selected from the compounds represented by the formulas (A), (B), (C), (F), (G) and (H):

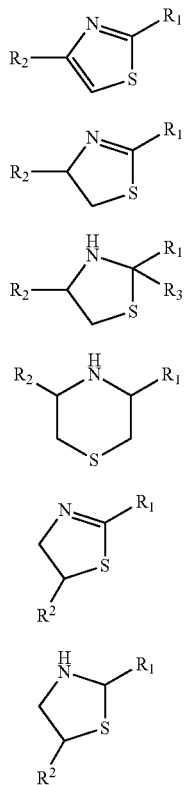

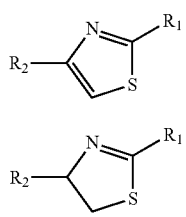

wherein

R₁ is hydrogen, a halogen atom (e.g., bromine atom), a $C_{1-6}$ alkyl group (e.g., methyl, ethyl) or a $C_{1-6}$ alkylthio group (e.g., methylthio), R₂ is hydrogen or a $C_{1-6}$ alkyl group (e.g., methyl), and R₃ is hydrogen or a $C_{1-6}$ alkyl group (e.g., methyl), or a salt thereof.

In the formulas (A), (B), (C), (F), (G) and (H), a compound wherein R₁, R₂ and R₃ are each independently hydrogen or a $C_{1-6}$ alkyl group (e.g., methyl, ethyl) or a salt thereof is more preferable.

Another preferable embodiment of the heterocyclic compound used as an active ingredient of the repellent of the present invention is a compound represented by the formula (A) or (B):

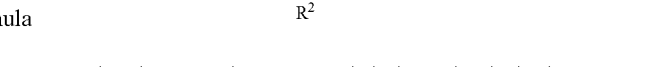

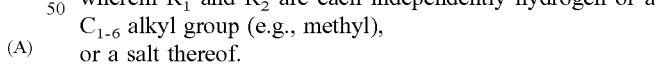

wherein

R₁ and R₂ are each independently hydrogen or a $C_{1-6}$ alkyl group (e.g., methyl, ethyl), and when one of R₁ and R₂ is hydrogen, the other is not hydrogen, or a salt thereof.

Another preferable embodiment of the heterocyclic compound used as an active ingredient of the repellent of the present invention is a compound represented by the formula (C):

wherein R₁, R₂ and R₃ are each independently hydrogen or a $C_{1-6}$ alkyl group (e.g., methyl)

or a salt thereof.

Another preferable embodiment of the heterocyclic compound used as an active ingredient of the repellent of the present invention is a compound represented by the formula (G):

wherein R₁ and R₂ are each independently hydrogen or a $C_{1-6}$ alkyl group (e.g., methyl)

or a salt thereof.

A compound of the formula (G) wherein, when one of R₁ and R₂ is hydrogen, the other is not hydrogen, or a salt thereof is more preferable.

Another preferable embodiment of the heterocyclic compound used as an active ingredient of the repellent of the present invention is a compound represented by the formula (H):

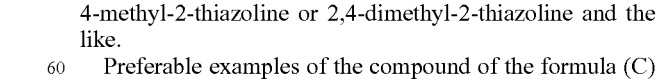

wherein R₁ and R₂ are each independently hydrogen or a $C_{1-6}$ alkyl group (e.g., methyl), or a salt thereof.

Preferable examples of the compound of the formula (A) include 2-methylthiazole, 2-ethylthiazole, 2-bromothiazole, 4-methylthiazole or 2,4-dimethylthiazole and the like.

Preferable examples of the compound of the formula (B) include 2-methyl-2-thiazoline, 2-methylthio-2-thiazoline, 4-methyl-2-thiazoline or 2,4-dimethyl-2-thiazoline and the like.

Preferable examples of the compound of the formula (C) include thiazolidine, 2-methylthiazolidine, 2,2-dimethylthiazolidine, 4-methylthiazolidine or 2,4-dimethylthiazolidine and the like.

Preferable examples of the compound of the formula (D) include 5,6-dihydro-4H-1,3-thiazine, 2-methyl-5,6-dihydro-4H-1,3-thiazine or 2,4-dimethyl-5,6-dihydro-4H-1,3-thiazine and the like.

Preferable examples of the compound of the formula (E) include 1,3-thiazane, 2-methyl-tetrahydro-1,3-thiazine or 2,4-dimethyl-tetrahydro-1,3-thiazine and the like.

Preferable examples of the compound of the formula (F) include thiomorpholine and the like.

Preferable examples of the compound of the formula (G) include 2,5-dimethyl-2-thiazoline or 5-methyl-2-thiazoline and the like.

Preferable examples of the compound of the formula (H) include 5-methylthiazolidine and the like.

A compound having an odor innately inducing fear in animals (hereinafter to be also referred to as the compound of the present invention) is not limited to the above-mentioned heterocyclic compound, and may be a compound having a chain structure and free of a ring (hereinafter to be also referred to as a chain compound). The chain compound contains at least one hetero atom selected from a nitrogen atom, a sulfur atom and an oxygen atom. Preferable examples of the chain compound include a chain sulfide compound and alkyl isothiocyanate. Preferable examples of the aforementioned chain sulfide compound include, but are not limited to, allyl methyl sulfide and the like. Preferable examples of the aforementioned alkyl isothiocyanate include, but are not limited to, $C_{1-6}$ alkyl isothiocyanate such as ethyl isothiocyanate and the like.

The salt of the compound of the present invention includes any salt as long as it is pharmaceutically or agriculturally, or industrially acceptable. For example, alkali metal salts such as sodium salt and potassium salt; alkaline earth metal salts such as magnesium salt and calcium salt; ammonium salts such as dimethylammonium salt and triethylammonium salt; inorganic acid salts such as hydrochloride, perchlorate, sulfate and nitrate; organic acid salts such as acetate and methanesulfonate; and the like can be mentioned.

The compound of the present invention can be preferably used as an active ingredient of an animal repellent. The aforementioned compound can be directly used as an active ingredient, or formulated into a liquid, a powder, a granule, a solid, a sheet and the like, and used after processing into a known form of a repellent. These preparations can be prepared by using additives generally used for formulation and a method generally used in the fields of pharmaceutical, pesticide, food and the like. Furthermore, these preparations are preferably formulated into a preparation with sustained odor. The preparation with sustained odor includes, for example, a sustained release preparation, a controlled release preparation and the like. Examples of the aforementioned additive include, but are not limited to, a surfactant, an organic solvent, a polymer material and the like.

As the aforementioned surfactant, anionic surfactant, nonionic surfactant, and amphoteric surfactant can be mentioned. Examples of the anionic surfactant include alkylbenzenesulfonate, alkanesulfonate, olefinsulfonate, monoalkyl sulfuric acid ester salt, polyoxyethylene alkyl ether sulfuric acid ester salt, polyoxyethylene alkylphenyl ether sulfuric acid ester salt and the like. As these salts, alkali metal salts such as sodium salt, potassium salt and the like, alkanolamine salts such as monoethanolamine, diethanolamine, triethanolamine and the like, and the like can be mentioned. Examples of the nonionic surfactant include polyoxyethylene alkyl ether, polyoxyethylene alkylphenyl ether, polyoxyethylene-polyoxypropylene block copolymer and the like, which are represented by ethylene oxide adducts of nonylphenyl ether and higher alcohol. As the amphoteric surfactant, betaine type amphoteric surfactants such as alkylbetaine, alkylamidobetaine, carbobetaine, hydroxysulfobetaine and the like, imidazoline type amphoteric surfactants and the like can be mentioned. One or more kinds of these surfactants can be selected and used.

Examples of the aforementioned organic solvent include solvents such as methanol, ethanol, propanol, isopropanol, ethylene glycol or propylene glycol, polymers thereof such as polyethylene glycol or polypropylene glycol, methylcellosolve, cellosolve, butylcellosolve, propylcellosolve, diethylene glycol, methylcarbitol, carbitol, butylcarbitol, propylcarbitol, propylene glycol monomethyl ether, propylene glycol monoethyl ether, propylene glycol monobutyl ether, propylene glycol monopropyl ether, dipropylene glycol, dipropylene glycol monomethyl ether, dipropylene glycol monoethyl ether, dipropylene glycol monobutyl ether, dipropylene glycol monopropyl ether, glycerol and derivatives thereof and the like. One or more kinds of the organic solvents can be selected and used.

The polymer material is not particularly limited as long as the effect as the repellent of the present invention is not impaired. For example, rubber materials such as silicone rubber, acrylic rubber, guar gum, locust bean gum, natural rubber, urethane rubber, ethylene-propylene rubber (EPR), ethylene-propylene-diene rubber (EPDM), styrene-butadiene rubber (SBR, SEBR and the like); synthetic polymers such as polyvinyl alkyl ether, polyvinyl alcohol, polyvinyl acetate, methyl vinyl ether/maleic anhydride copolymer, polyvinylpyrrolidone, carboxylvinyl polymer, vinylpyrrolidone/vinyl acetate alkylaminoacrylic acid copolymer, metacarboxybetaine/metacarboxy ester copolymer, styrene/maleic acid copolymer, ethylene/vinyl acetate copolymer, partially saponificated ethylene/vinyl acetate copolymer, partially saponificated polyvinyl acetate, polyethylene, polypropylene, polyethylene terephthalate, polybutylene terephthalate, polyamide, polyacetal, polyphenylene sulfide, polyimide, polyetherketone, polyetherimide, polyetheretherketone, polyacrylonitrile, poly(meth)acrylic acid alkyl ester, polyalkylene oxide and the like; natural polymer materials such as chitin, chitosan, starch, collagen, pullulan, ethylcellulose, methylcellulose, cellulose acetate, hydroxyethylcellulose, hydroxypropylcellulose, methylcellulose phthalate, carboxymethylcellulose and the like, and the like can be mentioned. One or more kinds of the polymer materials can be selected and used.

The repellent of the present invention can also be used, for example, as a solid agent obtained by adding the compound of the present invention to a gel substrate of the above-mentioned polymer materials, dispersing the compound well and molding same, or in a form of an aerosol.

Moreover, in the aforementioned repellent of the present invention, the compound of the present invention can also be impregnated in or carried on a porous substance. Examples of the porous substance include zeolite, porous silica, cellulose, heat-moisture treated starch, cyclodextrin, polyurethane foam, foamed polystyrene and the like. In addition, the repellent of the present invention or the compound of the present invention can also be used by being impregnated in, coated on or laminated on other substrates such as nonwoven fabric, rock wool, foamed urethane, paper, cotton, felt, rope, net and the like.

Where necessary, other repellent, and additives such as insect repellent, insecticide, antimicrobial agent, antifungal agent, flavor, colorant and the like can also be added.

The repellent of the present invention is useful for harmful animals in general that cause damage to farm products, forest, domestic animals or human habitation. Examples of the harmful animal include, but are not limited to, mammals such as mouse, mole, rabbit, weasel, deer, wild boar, monkey, cat, bear and the like, birds such as pigeon, crow and the like, reptiles such as snake and the like, and insects such as ant, centipede, grasshopper, cockroach and the like. It is particularly preferably used as a mice repellent and a deer repellent.

The "space from which the animal is repelled" means a habitation space of animals to be repelled or a space possibly invaded thereby; and examples include, but are not limited to, fields of rice and other crops, fruit farm, forest, breeding ground of domestic animals, road, expressway, railroad, airport, garbage collection point, park, garden, flower bed, parking place, building, house, kitchen, lavatory, veranda, storeroom, space under the floor, telephone pole, electric cable, communication cable, wire netting, fence and the like.

Examples of the method of placing a compound to be the active ingredient in a space from which an animal is repelled include, but are not limited to, a method of placing a composition containing a compound to be the active ingredient, a method of sprinkling, spraying, coating or volatilizing a compound to be the active ingredient and the like.

The concentration of the compound of the present invention in the repellent of the present invention can be appropriately determined according to the kind of the object animal, use place, formulation and the like, based on an experiment and the like. The ratio of the compound of the present invention and an additive is within the range of 0.0001:100 (W/W) to 100:0.0001 (W/W). When the ratio of the compound of the present invention is within the aforementioned range, the repellent effect on harmful animals can be sufficiently exhibited and maintained.

The present invention is explained in more detail in the following by referring to Examples and Experimental Examples, which are not to be construed as limitative.

EXAMPLES

Experimental Example 1: Freezing Test, Quantification of Fear Reaction Due to Odor About 5- to 7-month-old littermate wild-type mice (O-MACS-Cre) were placed in the mouse cages set in a draft (one mouse per cage) to perform habituation for 20 min. Similarly, 20 min habituation was performed the next day. On day 3, odor pods containing odorant molecules were placed in the cages in the draft, and the mice were placed in the cages with odor pods. The behaviors of the mice from day 1 to day 3 were video-recorded and the freezing time was analyzed by FreezeFrame system manufactured by NeuroScience Inc. The time during which the mouse was motionless for 2 seconds or longer was measured as a freezing time, and the time of freezing during the 20 min observation time was shown in %. The freezing time on day 2 was shown as control without odor in the data. As the mice used for experiment, male mice were used to avoid abnormality in the olfactory sense due to the sexual cycle. Each experiment was performed with n=5. The odor pod refers to an apparatus containing filter paper impregnated with odorant and placed in a plastic petri dish with a lid having a hole. In this experiment, 2 MB (2-methylbutyric acid) 45 μL (270.6 μmol) or TMT 35 μL (270.6 μmol) was used as the odorant molecule.

The results of Experimental Example 1 are shown in FIG. 1. 2 MB is a substance showing a putrid odor, and TMT is a substance inducing a sense of fear. It was shown that TMT inducing a sense of fear afforded a longer freezing time.

Example 1

Using various compounds, the freezing test shown in Experimental Example 1 was performed. The experiment was performed with n=6 for each compound, and the t-test was performed using the data without odor and the data with various odor smells. * shows $p<0.05$,  shows $p<0.01$, and * shows $p<0.001$. For the experiment, 270.6 μmol of odorant molecules were used. The abbreviations and the formal names of the odorant molecules used are as follows.

Figure 2:
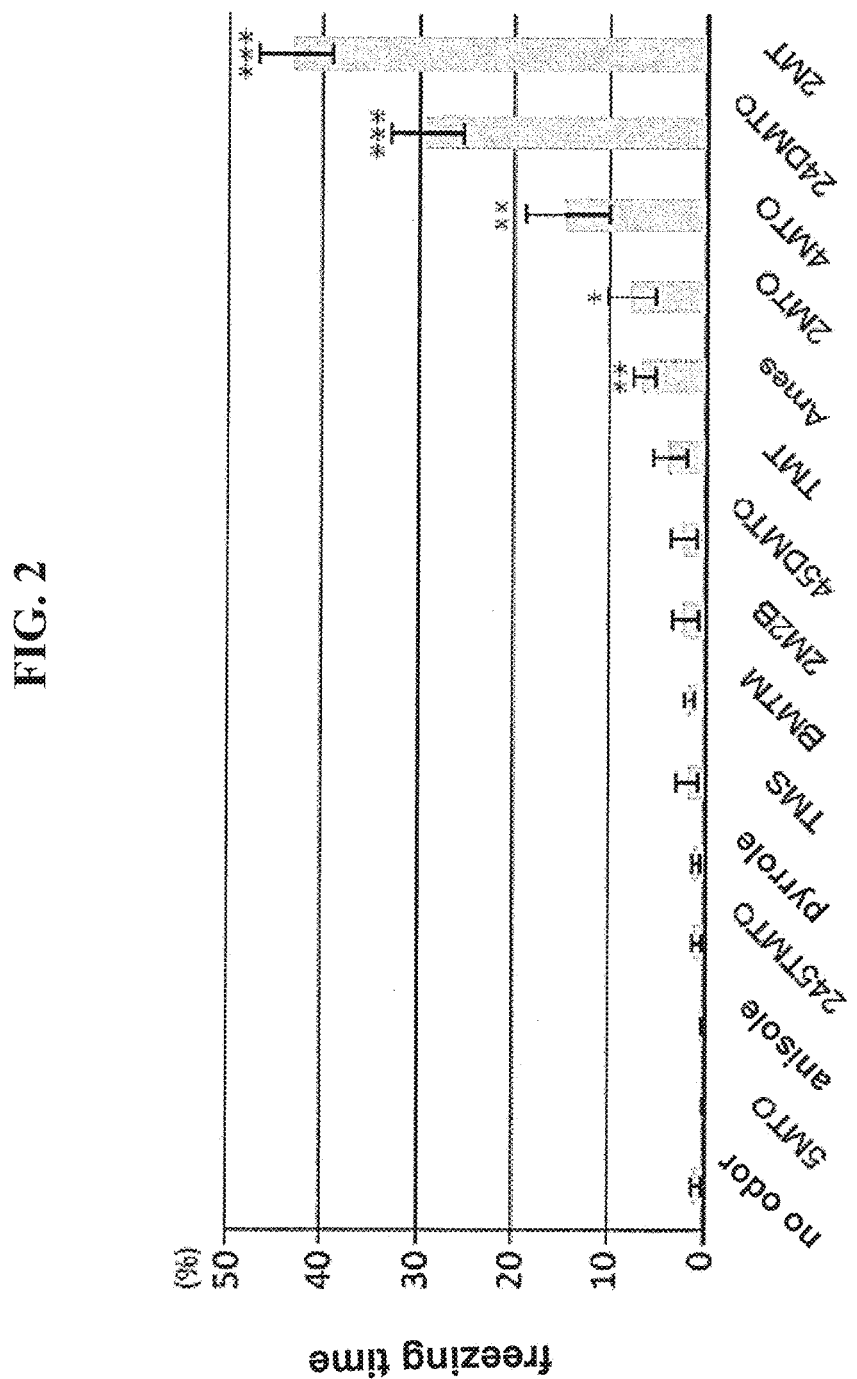
FIG. 2 shows the results of freezing tests using various compounds.

5MTO: 5-methylthiazole
245TMTO: 2,4,5-trimethylthiazole
TMS: trimethylene sulfide
BMTM: bis(methylthio)methane
2M2B: 2-methyl-2-butanediol
45DMTO: 4,5-dimethylthiazole
TMT: 2,4,5-trimethyl-3-thiazoline
Ames: allyl methyl sulfide
2MTO: 2-methylthiazole
4MTO: 4-methylthiazole
24DMTO: 2,4-dimethylthiazole
2MT: 2-methyl-2-thiazoline The results of Example 1 are shown in FIG. 2. Thiazoles and thiazoline wherein the 2-position and/or the 4-position are/is substituted showed a higher effect as compared to TMT.

Example 2

Activation Pattern of Glomeruli in the Dorsal Olfactory Bulb Activated by Various Compounds (Intrinsic Optical Signal Imaging Method)

The activation patterns of glomeruli in the dorsal olfactory bulb activated by various odors used for freezing test were analyzed by the intrinsic optical signal imaging method described in Nat. Neurosci 3: 1035-1043 (2000).

Figure 3:
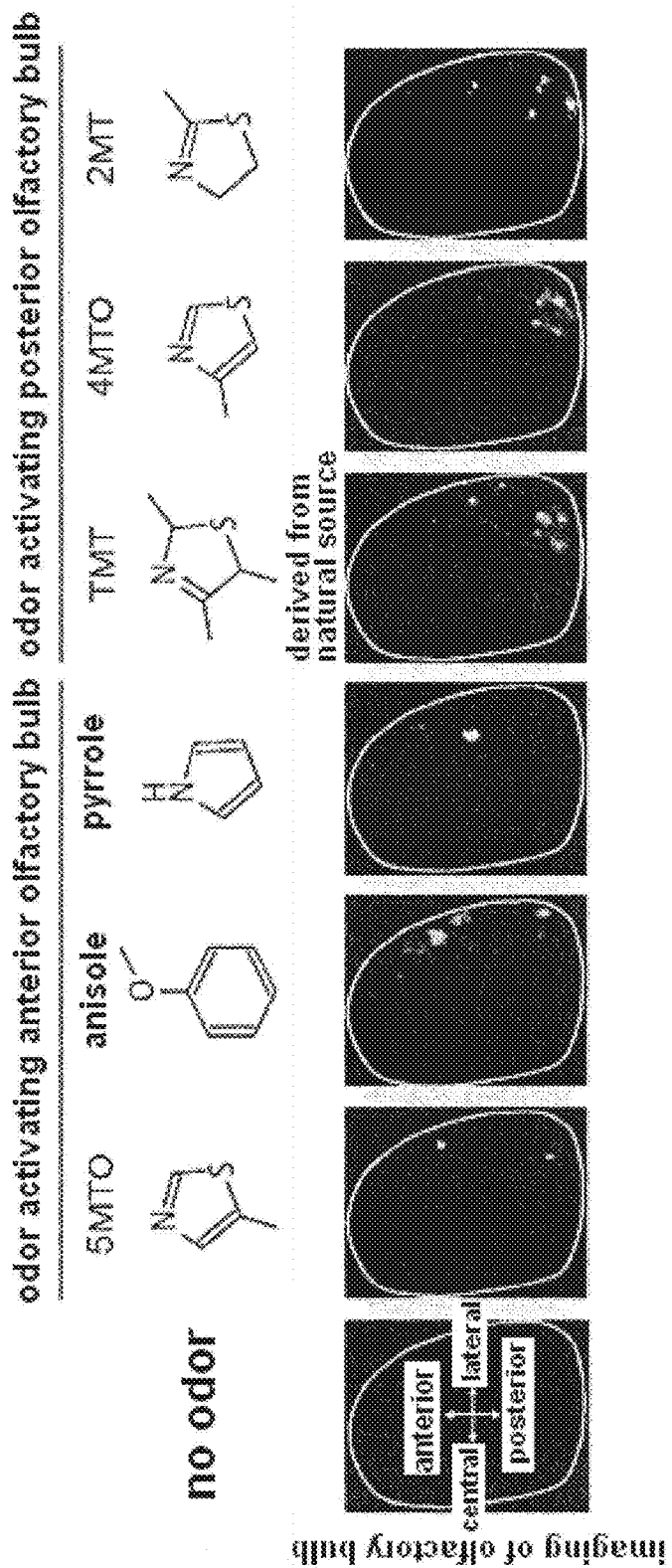
FIG. 3 shows the analysis results, by an intrinsic optical signal imaging method, of the activation patterns of glomeruli in the dorsal olfactory bulb activated by various odors used for the freezing tests.

The results of Example 2 are shown in FIG. 3. It has been suggested that, of the glomeruli activated by TMT in the dorsal olfactory bulb, the odorant molecule that activates frontal glomeruli is less effective for inducing freezing, and the odorant molecule that activates posterior glomeruli is highly effective for inducing freezing. While 5MTO, TMT, 4MTO and 2MT, which are all thiazole derivatives or thiazoline derivatives, the compounds wherein the 2-position or the 4-position is substituted activate posterior glomeruli, that is, have high repellent effects.

Example 3

Comparison of Results of Freezing Test at Various Concentrations

The influence of the concentration of the odorant molecule on the effect of inducing a freezing behavior was analyzed. A dilution series of the most effective 2MT and control TMT were prepared, and the level of freezing behavior induced by odor at each concentration was analyzed. The freezing behavior was analyzed by a method similar to that in Example 1. The amount of the odorant molecules used of the both compounds was 270.6 nmol for 0.001, 2.706 μmol for 0.01, 27.06 μmol for 0.1, 270.6 μmol for 1, and 1.082 mmol for 4. The odorant molecule concentration in the gas in the test system was measured by gas chromatography, and the presence of a dependency relationship between the amount of the odorant molecules used for the test and the odorant molecule concentration in the gas in the test system was confirmed.

Figure 4:
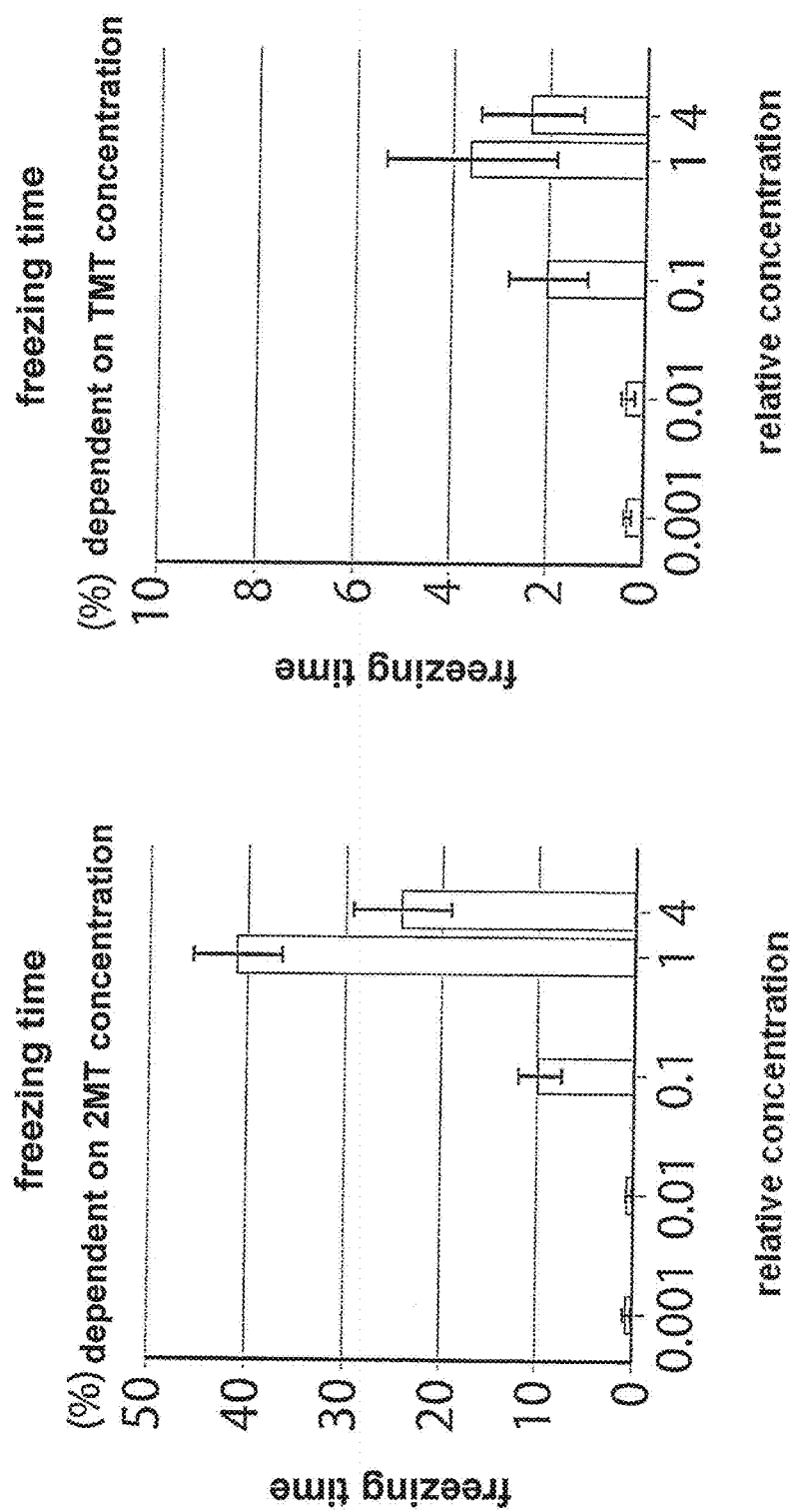
FIG. 4 shows the results of freezing tests at various concentrations of 2MT and TMT.

The results of Example 3 are shown in FIG. 4. 2MT at any concentration showed 5 to 10 times stronger effect than TMT. It was shown that TMT and 2MT at too high a concentration provided a decreased effect.

Example 4

Using the following test compounds (13 kinds), the freezing test shown in Experimental Example 1 was performed. The experiment was performed with n=8 for each compound, and the Student's t-test was performed using the data of an odorant compound (1,3-dioxolane) that does not induce a fear reaction and the data with various odor smells. * shows p<0.05,  shows p<0.01, and * shows p<0.001, each exhibiting a significant difference. For the experiment, 270.6 μmol of odorant compounds were used.

Test Compounds:
2,5-dimethyl-2-thiazoline
2MT: 2-methyl-2-thiazoline
5-methyl-2-thiazoline
2,2-dimethylthiazolidine
thiazolidine
thiomorpholine
ethyl isothiocyanate
2-ethylthiazole
2-methylthio-2-thiazoline
2-bromothiazole
isobutylene sulfide
5-methylthiazolidine
thiophene The results of Example 4 are shown in Table 1. All compounds showed a freezing behavior due to fear.

TABLE 1

| test compound | Freezing time (%) |
|---|---|
| 2,5-dimethyl-2-thiazoline | 55.9 ± 4.4*** |
| 2MT | 49.9 ± 3.0*** |
| 5-methyl-2-thiazoline | 39.6 ± 3.5*** |
| 2,2-dimethylthiazolidine | 29.3 ± 5.2*** |
| thiazolidine | 18.2 ± 5.3*** |
| thiomorpholine | 15.9 ± 2.5*** |
| ethyl isothiocyanate | 14.0 ± 4.5* |
| 2-ethylthiazole | 7.3 ± 1.6** |
| 2-methylthio-2-thiazoline | 6.2 ± 3.0 |
| 2-bromothiazole | 4.8 ± 1.6* |
| isobutylene sulfide | 4.3 ± 1.9* |
| 5-methylthiazolidine | 4.2 ± 2.7 |
| thiophene | 2.7 ± 1.6 |

Each value shows freezing time (%)±standard error.

Example 5

Acclimation test: By the method of Experimental Example 1, mice (N=8) were forced to smell the test compound (2MT) every day for 8 days, and the freezing time (%) was measured over time. As a control, mice that were forced to learn to feel fear with the smell of anisole by a method including applying an electric shock immediately after smelling anisole (hereinafter to be also referred to as fear learning mice) were used. The aforementioned fear learning mice (N=8) were forced to smell anisole every day for 8 days, and the freezing time (%) was measured over time. Student's t-test was performed using the freezing time on day 1 and the freezing time on day 2 ff. * shows p<0.05,  shows p<0.01, and * shows p<0.001, each exhibiting a significant difference.

Figure 5:
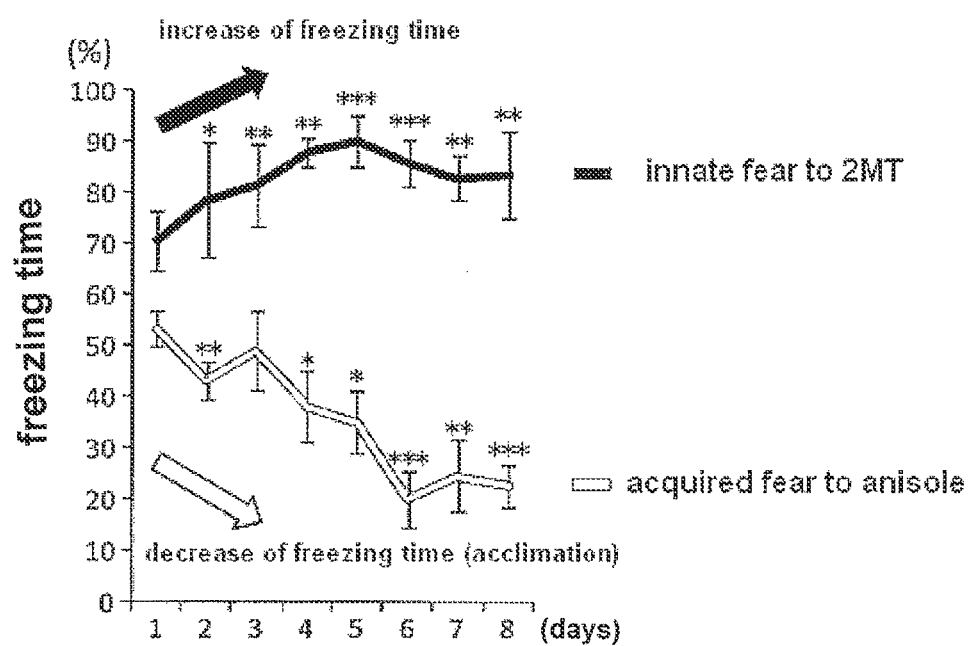
FIG. 5 shows the results of acclimation tests of an odor inducing fear (Example 5). In the Figure, the black line shows the freezing time profile with the smell of 2MT, the white line shows the freezing time profile of a mouse with the smell of anisole, after fear learning of the mouse with the odor of anisole, and each value shows mean±standard error.

The results of Example 5 are shown in FIG. 5. When the mice smelled 2MT every day for 8 days, the freezing time did not decrease but rather increased. The results mean that the odor of 2MT is an odor of innate fear programmed in the gene of the mouse, and mean the absence of acclimation of the mouse to 2MT that induces innate fear. On the other hand, in the mice that underwent fear learning with anisole, the freezing time with anisole was not less than 50% the next day. However, when the mice smelled the odor every day, the freezing time decreased with time. This means acclimation of the mouse to the odor that induces fear by acquired learning of fear.

Example 6

A deer was lured with feed to confirm that it was attracted to feed, and the response of the deer to feed containing the repellent of the present invention was confirmed. Although with slight individual differences, it was confirmed that the repellent of the present invention showed a very high repellent effect for deer from young deer to mature deer, regardless of male and female. In a place where a feeding damage by deer has actually occurred, a wire netting with 3 holes A, B and C is set in the route where deer appear frequently, and the repellent effect is confirmed based on the changes in the number of deer that pass through the hole when the repellent is set in any of the holes A, B and C.

Example 7

The repellent of the present invention is set in 2×3 m veranda and on the handrail therein where pigeons regularly fly in to pollute the place, and fine granule corn (100 g) is placed on the floor of the veranda. The residual amount of the feed is measured over time to determine the repellent rate (%).

Example 8

In a chestnut orchard where wild boar appears frequently, the repellent of the present invention is set at about 30 cm above the ground in one test area (4×10 m). Sweet potatoes (about 2 kg) are buried near the surface of the ground at the center of each area, and each residual amount is measured after a given time to determine the repellent rate.

Example 9

A commercially available cat food (boiled tuna flakes, about 95 g) is placed in a circular plastic container (diameter 25 cm, height 7 cm), and the repellent of the present invention is set. The residual ratio of the cat food in each container is measured at given time intervals.

Example 10

The repellent of the present invention is set near a polyethylene bag containing garbage (about 1 kg), they are left together with a non-treated bag in a garbage collection point where stray dogs, stray cats and crow appear frequently, and the bag tearing state of the non-treated area and the treated area over two nights is confirmed.

INDUSTRIAL APPLICABILITY

The present invention is directed to an animal repellent containing, as an active ingredient, a compound having an odor innately inducing fear in animals. Since the animal repellent can prevent damage by harmful small animals, for example, it can be utilized in the fields of agriculture, forestry, transportation (expressway, railroad, and airplane), communication industry and the like.

This application is based on patent application Nos. 2010-25681 and 2010-172671 filed in Japan, the contents of which are incorporated herein by reference in their entirety.

The invention claimed is:

1. A method for repelling a mammal, comprising placing a compound selected from the compounds represented by the formulas (A), (D), (E), (F), (G) and (H):

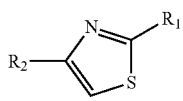 (A)

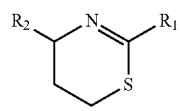 (D)

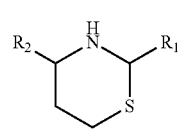 (E)

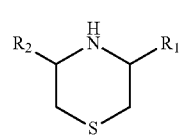 (F)

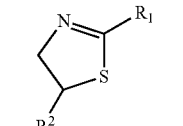 (G)

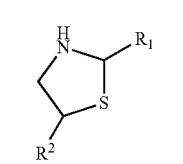 (H)

wherein $R_1$ and $R_2$ are each independently hydrogen, a halogen atom, methyl, ethyl, or a $C_{1-6}$ alkylthio group, or a salt thereof, in a space from which the mammal is repelled.

2. The method according to claim 1, wherein said compound is a compound represented by the formula (A).

3. The method according to claim 2, wherein said compound is a compound selected from 2-methylthiazole, 2-ethylthiazole, 2-bromothiazole, 4-methylthiazole, and 2,4-dimethylthiazole.

4. The method according to claim 3, wherein said compound is 2-methylthiazole.

5. The method according to claim 3, wherein said compound is 2-ethylthiazole.

6. The method according to claim 3, wherein said compound is 2-bromothiazole.

7. The method according to claim 3, wherein said compound is 4-methylthiazole.

8. The method according to claim 3, wherein said compound is 2,4-dimethylthiazole.

9. The method according to claim 1, wherein said compound is a compound represented by the formula (F).

10. The method according to claim 9, wherein said compound is thiomorpholine.

11. The method according to claim 1, wherein said compound is a compound represented by the formula (G).

12. The method according to claim 11, wherein said compound is a compound selected from 2,5-dimethyl-2-thiazoline and 5-methyl-2-thiazoline.

13. The method according to claim 12, wherein said compound is 2,5-dimethyl-2-thiazoline.

14. The method according to claim 12, wherein said compound is 5-methyl-2-thiazoline.

15. The method according to claim 1, wherein the mammal is a harmful mammal.

* * * * *